US012575962B1

(12) United States Patent
Koeckert

(10) Patent No.: US 12,575,962 B1
(45) Date of Patent: Mar. 17, 2026

(54) URINARY WASTE SYSTEM

(71) Applicant: Helmut Koeckert, Lakewood, CO (US)

(72) Inventor: Helmut Koeckert, Lakewood, CO (US)

( * ) Notice: Subject to any disclaimer, the term of this patent is extended or adjusted under 35 U.S.C. 154(b) by 0 days.

(21) Appl. No.: 18/926,049

(22) Filed: Oct. 24, 2024

(51) Int. Cl.
  *A61F 5/455* (2006.01)
  *A61B 10/00* (2006.01)
  *A61F 5/44* (2006.01)

(52) U.S. Cl.
  CPC ............ *A61F 5/455* (2013.01); *A61F 5/4408* (2013.01); *A61B 10/007* (2013.01); *A61F 5/4556* (2013.01)

(58) Field of Classification Search
  CPC ...... A61F 5/455; A61F 5/4408; A61F 5/4556; A61B 10/007
  See application file for complete search history.

(56) References Cited

U.S. PATENT DOCUMENTS

| | | | | |
|---|---|---|---|---|
| 2,490,969 A | * | 12/1949 | Kinyon | A61F 5/455 |
| | | | | 4/144.3 |
| 3,077,883 A | * | 2/1963 | Hill | A61F 5/451 |
| | | | | 604/347 |
| 3,131,403 A | * | 5/1964 | Hill | A61F 5/455 |
| | | | | D24/118 |
| 3,194,238 A | * | 7/1965 | Breece, Jr. | A61F 5/455 |
| | | | | D24/112 |
| 3,335,714 A | * | 8/1967 | Giesy | A61B 10/007 |
| | | | | D24/117 |

| | | | | |
|---|---|---|---|---|
| 3,349,768 A | * | 10/1967 | Keane | A61F 5/455 |
| | | | | 604/347 |
| 3,406,690 A | * | 10/1968 | Igel | A61F 5/451 |
| | | | | 600/580 |
| 3,459,174 A | * | 8/1969 | Walker | A61B 10/007 |
| | | | | 600/574 |

(Continued)

FOREIGN PATENT DOCUMENTS

| | | | | |
|---|---|---|---|---|
| CN | 116509619 A | * | 8/2023 | |
| DE | 3327444 A | * | 2/1984 | A61B 10/007 |

(Continued)

OTHER PUBLICATIONS

Spouti product description. Retrieved on Oct. 24, 2024 from https://myspouti.com/.

(Continued)

*Primary Examiner* — Sean P Dougherty
(74) *Attorney, Agent, or Firm* — HOLZER PATEL DRENNAN

(57) ABSTRACT

Systems for collecting and removing urinary waste from a user. One such system includes a urinary waste receptacle defined by a concave dome-shaped shell and an opposite concave wall, the shell and wall defining an interior volume. An aperture in the wall defines a urinary waste inlet fluidly connected to the interior volume, the aperture having a deformable dam-like structure at least partially therearound and a cross-sectional area of the urinary waste inlet is smaller than a maximum cross-sectional area of the urinary waste receptacle. The receptacle has a waste outlet fluidly connected to the interior volume. A tubular structure may facilitate flow of the urinary waste from the inlet to the outlet. Included is a harness attached to the urinary waste receptacle to position the waste receptacle against a genital region of the user.

18 Claims, 12 Drawing Sheets

(56)                References Cited

U.S. PATENT DOCUMENTS

| | | | | |
|---|---|---|---|---|
| RE26,854 E | * | 4/1970 | Giesy | A61B 10/007 600/574 |
| 3,512,185 A | * | 5/1970 | Ellis | A61F 5/455 4/144.3 |
| 3,522,808 A | * | 8/1970 | Worcester | A61F 5/4401 604/350 |
| 3,583,388 A | * | 6/1971 | Hovick | A61B 10/007 600/574 |
| 3,722,503 A | * | 3/1973 | Hovick | A61F 5/44 4/144.3 |
| 3,750,647 A | * | 8/1973 | Gleason | A61B 10/007 4/144.3 |
| 3,750,648 A | * | 8/1973 | Gleason | A61B 10/007 4/144.3 |
| 3,964,111 A | * | 6/1976 | Packer | A61F 5/4556 604/327 |
| 4,023,216 A | * | 5/1977 | Li | A61F 5/4556 4/144.1 |
| 4,094,020 A | * | 6/1978 | Franklin | A61F 5/44 4/144.1 |
| 4,106,490 A | * | 8/1978 | Spilman | A61B 10/007 604/347 |
| 4,139,006 A | * | 2/1979 | Corey | A61F 2/005 604/48 |
| 4,194,508 A | * | 3/1980 | Anderson | A61F 5/455 4/144.3 |
| 4,198,979 A | * | 4/1980 | Cooney | A61F 5/455 604/329 |
| 4,202,058 A | * | 5/1980 | Anderson | A61G 9/006 604/347 |
| 4,301,812 A | * | 11/1981 | Layton | A61B 10/007 73/863.52 |
| 4,553,968 A | | 11/1985 | Komis | |
| 4,563,183 A | | 1/1986 | Barrodale et al. | |
| 4,568,339 A | * | 2/1986 | Steer | A61F 5/455 4/144.3 |
| 4,692,160 A | * | 9/1987 | Nussbaumer | A61F 5/455 604/331 |
| 4,756,029 A | * | 7/1988 | Zieve | A61F 5/4556 4/144.1 |
| 4,769,215 A | * | 9/1988 | Ehrenkranz | A61B 10/007 73/863.52 |
| 4,815,151 A | * | 3/1989 | Ball | A61F 5/4556 4/144.1 |
| 4,838,883 A | * | 6/1989 | Matsuura | A61F 5/4408 604/353 |
| 4,846,818 A | * | 7/1989 | Keldahl | A61F 5/455 600/574 |
| 4,846,819 A | * | 7/1989 | Welch | A61F 5/455 604/336 |
| 4,889,533 A | * | 12/1989 | Beecher | A61F 5/4407 604/355 |
| 4,911,698 A | * | 3/1990 | Wapner | A61B 10/007 4/144.3 |
| 5,002,541 A | * | 3/1991 | Conkling | A61F 5/44 604/324 |
| 5,004,463 A | * | 4/1991 | Nigay | A61F 5/455 604/327 |
| 5,069,878 A | * | 12/1991 | Ehrenkranz | A61B 10/007 73/863.52 |
| 5,267,988 A | * | 12/1993 | Farkas | A47K 11/12 4/144.3 |
| 5,329,644 A | * | 7/1994 | Scott | A61F 5/4556 4/144.2 |
| 5,387,205 A | * | 2/1995 | Cummins | A61B 10/007 4/144.3 |
| 5,593,389 A | * | 1/1997 | Chang | A61M 25/02 604/177 |
| 5,894,608 A | * | 4/1999 | Birbara | A61F 5/4556 604/319 |
| 6,592,560 B2 | * | 7/2003 | Snyder | A61F 5/4553 604/544 |
| 6,904,621 B2 | * | 6/2005 | Otto | A61F 5/451 4/144.1 |
| 7,135,012 B2 | | 11/2006 | Harvie | |
| 7,181,781 B1 | * | 2/2007 | Trabold | A61F 5/455 4/144.1 |
| 7,931,634 B2 | | 4/2011 | Swiecicki et al. | |
| 8,690,846 B2 | | 4/2014 | Chen et al. | |
| 9,254,218 B2 | | 2/2016 | Newton | |
| 10,238,530 B2 | | 3/2019 | Mahalingam | |
| 10,568,756 B1 | * | 2/2020 | Heckerman | A61F 5/4553 |
| 11,583,434 B1 | * | 2/2023 | Cimino | A61F 5/4556 |
| 11,666,474 B2 | | 6/2023 | Cohn et al. | |
| 2002/0026161 A1 | * | 2/2002 | Grundke | A61F 5/455 604/327 |
| 2002/0193760 A1 | * | 12/2002 | Thompson | A61F 5/4556 604/347 |
| 2003/0181880 A1 | | 9/2003 | Schwartz | |
| 2003/0233079 A1 | * | 12/2003 | Parks | A61F 5/4556 604/355 |
| 2004/0098794 A1 | * | 5/2004 | Ernest | A47K 11/12 4/144.2 |
| 2004/0162535 A1 | * | 8/2004 | Preston | A61F 5/455 604/329 |
| 2005/0010182 A1 | * | 1/2005 | Parks | A61F 5/4556 604/355 |
| 2005/0137557 A1 | * | 6/2005 | Swiecicki | A61F 5/455 604/385.17 |
| 2006/0149195 A1 | * | 7/2006 | Oprandi | A61F 5/4556 604/329 |
| 2006/0155214 A1 | * | 7/2006 | Wightman | A61F 5/455 600/574 |
| 2007/0044213 A1 | * | 3/2007 | Hall | A61F 5/4556 4/144.4 |
| 2007/0270716 A1 | * | 11/2007 | Wu | A61B 5/20 600/580 |
| 2008/0177201 A1 | * | 7/2008 | Deadwyler | A61B 10/007 604/347 |
| 2008/0183102 A1 | * | 7/2008 | Dunkin | A61B 10/007 600/580 |
| 2008/0300448 A1 | * | 12/2008 | Frazier | A61F 5/455 600/29 |
| 2010/0185168 A1 | * | 7/2010 | Graauw | A61F 5/4556 604/347 |
| 2010/0312204 A1 | * | 12/2010 | Sheu | A61F 5/4408 604/330 |
| 2010/0331798 A1 | * | 12/2010 | Block | A61F 5/4556 604/329 |
| 2011/0028922 A1 | | 2/2011 | Kay et al. | |
| 2011/0030130 A1 | * | 2/2011 | Stein | A61F 5/4556 4/144.2 |
| 2011/0270203 A1 | * | 11/2011 | Sharpe | A61F 5/451 604/326 |
| 2012/0117720 A1 | * | 5/2012 | King-Boutte | A61F 5/4556 4/144.2 |
| 2012/0210502 A1 | * | 8/2012 | Baham | A61F 5/4556 4/144.3 |
| 2014/0033414 A1 | * | 2/2014 | Kolter | A47K 11/12 4/144.3 |
| 2014/0325746 A1 | * | 11/2014 | Block | A61F 5/453 4/144.3 |
| 2015/0157300 A1 | * | 6/2015 | Ealovega | A61B 10/007 422/417 |
| 2015/0223784 A1 | * | 8/2015 | Van Damme | A61F 5/4405 73/864.63 |
| 2015/0359660 A1 | * | 12/2015 | Harvie | A61F 5/441 604/351 |
| 2017/0007438 A1 | * | 1/2017 | Harvie | A61F 5/453 |
| 2017/0273818 A1 | * | 9/2017 | Pryor | A61F 5/4556 |
| 2017/0281399 A1 | * | 10/2017 | VanMiddendorp | A61M 1/80 |
| 2017/0312116 A1 | | 11/2017 | Laniado | |
| 2017/0325641 A1 | * | 11/2017 | Rudolph | A61F 5/4556 |
| 2017/0325788 A1 | * | 11/2017 | Ealovega | A61B 10/007 |
| 2017/0340475 A1 | | 11/2017 | Joh | |
| 2020/0046544 A1 | * | 2/2020 | Godinez | A61F 5/455 |
| 2020/0085610 A1 | * | 3/2020 | Cohn | A61F 5/451 |
| 2020/0146872 A1 | | 5/2020 | Jia | |
| 2020/0229964 A1 | * | 7/2020 | Staali | A61F 5/4405 |

(56)                    References Cited

U.S. PATENT DOCUMENTS

| 2020/0323519 | A1* | 10/2020 | Ealovega | A61B 10/0096 |
|---|---|---|---|---|
| 2020/0375781 | A1* | 12/2020 | Staali | A61M 1/71 |
| 2020/0375787 | A1* | 12/2020 | Wang | A61F 5/4408 |
| 2021/0145625 | A1* | 5/2021 | Cooks | A61F 5/455 |
| 2021/0186787 | A1* | 6/2021 | Ordinanza | A61F 5/44 |
| 2021/0315726 | A1* | 10/2021 | Lin | A61F 5/4408 |
| 2021/0353450 | A1* | 11/2021 | Sharma | A61F 5/4408 |
| 2021/0353473 | A1* | 11/2021 | Yi | A61F 5/4553 |
| 2021/0361917 | A1* | 11/2021 | Edwards | A61F 5/4408 |
| 2022/0031213 | A1 | 2/2022 | Stevens et al. | |
| 2022/0031290 | A1* | 2/2022 | Weed | A61B 10/007 |
| 2022/0087853 | A1* | 3/2022 | Farrar | A61F 5/455 |
| 2022/0104965 | A1* | 4/2022 | Vaninetti | A61M 1/71 |
| 2022/0257406 | A1* | 8/2022 | Snow | A61F 5/4553 |
| 2023/0404790 | A1* | 12/2023 | Wolfe | A61F 5/4405 |
| 2024/0164937 | A1* | 5/2024 | Gloeckner | A61F 5/455 |
| 2024/0207084 | A1* | 6/2024 | Stead | A61G 9/006 |
| 2024/0307214 | A1* | 9/2024 | Liu | A61F 5/455 |
| 2025/0099288 | A1* | 3/2025 | Harvie | A61F 5/451 |

FOREIGN PATENT DOCUMENTS

| DE | 202017104969 | U1 * | 7/2018 | A61F 5/4408 |
|---|---|---|---|---|
| EP | 0018749 | A1 * | 4/1980 | A61F 5/44 |
| GB | 2124072 | B | 8/1984 | |

OTHER PUBLICATIONS

"The PureWick Flex Female External Catheter", Product description. Retrieved on Oct. 24, 2024 from https://www.purewickathome.com/purewick-for-female.html.

* cited by examiner

202

A dimension
of waste inlet

210

214

212

A dimension
of receptacle

208

Area of
waste inlet

216

Area of
receptacle

204

900

928          906

902

URINARY WASTE SYSTEM

BACKGROUND

Systems to collect and dispose of urinary waste from women have included devices such as diapers and bedpans. Diapers may be convenient in that they are wearable under the clothing, but they are often unsanitary and uncomfortable as the urine is not sufficiently transported away from the woman's skin and without prompt changing, the urine is left to reside next to the woman. Bedpans are able to transport urine somewhat away from the woman but may be inconvenient to use and may not be ready to use without warning. Furthermore, bedpans may not be discreet, and may be undesirable for non-ambulatory women due to their bulkiness. Both devices are subject to leakage or spillage if not used properly.

SUMMARY

Described herein are various systems and devices for collecting, separating and removing urinary waste for a user's body (e.g., a woman's body). One such system includes a urinary waste receptacle having a urinary waste inlet with a perimeter at least partially lined with a deformable seal, wherein a cross-sectional area of the urinary waste inlet is smaller than a maximum cross-sectional area of the urinary waste receptacle. The urinary waste inlet is configured to align with a urethral opening of the user when the urinary waste receptacle is positioned to collect the urinary waste from the urethral opening during urination by the user. The receptacle has a waste outlet from the urinary waste receptacle to remove the urinary waste from the urinary waste receptacle, the waste flow aided by fluid pressure and by gravity. Present within the receptacle can be a tubular structure that facilitates the flow of waste from the inlet to the outlet. The system can include a harness attached to the urinary waste receptacle configured to pull the deformable seal against a genital region of the user to form an interface between the deformable seal and skin of the genital region around the urethral opening of the user.

By use of the term "receptacle" herein, it is not intended that the device retains or stores urinary waste or other waste, but that the device has a volume providing a conduit therethrough for the waste.

One particular waste receptacle having two conduits (e.g., tubes or tubular structures) present within the receptacle, with one conduit having a larger inlet located at a higher position within the receptacle and a second inlet lower in the receptacle connecting to a second conduit. The first conduit is configured to carry a larger volume, and optionally more forceful, waste stream; due to its greater volume and flow rate, this waste stream will bypass the second, lower inlet of the second conduit. The second inlet will receive any waste flow having a reduced pressure and/or volume. Regardless of the flow, both conduits can accommodate any variation in a urinary cycle. The flow from the conduits may exit via a single or separate outlets.

Techniques described herein include methods of using a system for collecting and removing urinary waste from a user. One such method includes aligning a urinary waste receptacle with a urethral opening of the user, the urinary waste receptacle forming a urinary waste inlet having a perimeter at least partially lined with a deformable seal, wherein a cross-sectional area of the urinary waste inlet is smaller than a maximum cross-sectional area of the urinary waste receptacle and the urinary waste receptacle is configured to be positioned to collect the urinary waste from the urethral opening during urination by the user and a waste outlet extends from the urinary waste receptacle, the waste outlet being configured to remove the urinary waste from the urinary waste receptacle, and maintaining the alignment of the urinary waste receptacle for at least a portion of urination by the user to collect urine into the urinary waste receptacle. The method may include equipping a harness around the user, wherein the harness is attached to the urinary waste receptacle, to retain the urinary waste receptacle in a position to accept urinary waste. The harness may be configured to pull the deformable seal against a genital region of the user to form an interface between the deformable seal and skin of the genital region around the urethral opening of the user. The urinary waste receptacle is configured to remain external of the genital region of the user.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

Other implementations are also described and recited herein.

BRIEF DESCRIPTIONS OF THE DRAWING

DETAILED DESCRIPTION

Figure 1:
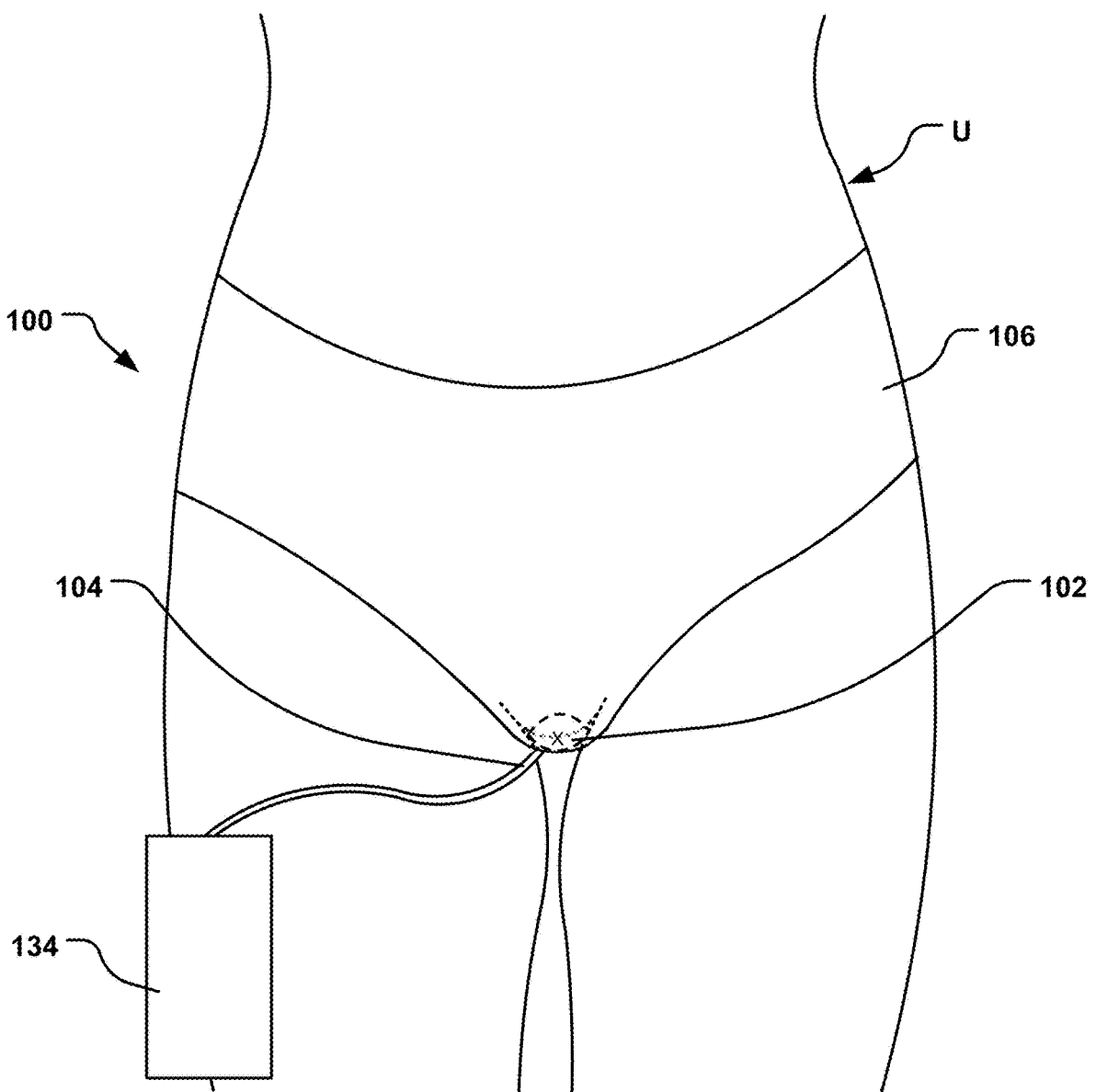
FIG. 1 illustrates an example urinary collection system positioned on a user.

Designers of systems for collection of urinary waste generally face challenges in making the device comfortable, discrete, and effective. Because the device may be worn for long periods of time, a comfortable design for the device will enhance the overall experience of using the device and decrease fatigue associated with wearing it. Users may desire a discrete design for the device to reduce the impact of the device on the appearance of the user.

In the field of automatic urinary waste collection, challenges to designing an effective device include reducing the risk of leakage from the device, especially on the boundary between the device and the skin of the user, quickly sensing and/or removing waste excreted by the user, and reducing the hassle for the user associated with using and maintaining the device.

The following description provides various examples, designs and implementations of urinary collection systems having a urinary waste receptacle configured to be positioned to collect urinary waste from the urethral opening during urination by a user.

In the following description, reference is made to the accompanying drawing that forms a part hereof and in which is shown by way of illustration at least one specific implementation. The following description provides additional specific implementations. It is to be understood that other implementations are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples, including the figures, provided below. In some instances, a reference numeral may have an associated sub-label consisting of a lower-case letter to denote one of multiple similar components. When reference is made to a reference numeral without specification of a sub-label, the reference is intended to refer to all such multiple similar components.

FIG. 1 illustrates an example urinary collection system 100 in use by a person or user U. The urinary collection system 100 collects and removes the urinary waste from the user U. The urinary collection system 100 has a urinary waste receptacle 102, a waste outlet 104 therefrom, and a harness 106. The urinary waste receptacle 102 may take the form of a substantially concave dome-shaped shell defining an interior volume that collects urinary waste from the user U; that urinary waste is removed via the waste outlet 104.

All elements of the system 100 are configured to remain external to the genital region of the user; no portion of the urinary waste receptacle 202 enters the urethral opening or the vaginal opening. The urinary waste receptacle 102 has a physical configuration that contours the curve of the genital region. The urinary waste receptacle 102 may be designed to have a reduced size, which may allow the device to be more discrete.

The urinary waste receptacle 102 can be held in proper position on the user by the harness 106, which is configured to pull the receptacle 102 against the genital region of the user. The harness 106 is configured to be comfortable to wear, such as by being made out of a soft or pleasant material or by including materials configured to stretch to the shape of the individual user's body. The harness 106 may include adjustable straps or another adjustment mechanism configured to allow the user to adjust the location of the urinary waste receptacle 102. The harness 106 has minimal seams, buckles, latches, etc. that could form pressure points on the user's body. The harness 106 may have a shape that is the same as or different than that of the receptacle 102; for example, the portion of the harness 106 directly engaging with an oval receptacle 102 may be oval or rectangular.

Also seen in FIG. 1, the urinary collection system 100 may include a pressure modulator 134 positioned in-line with the waste outlet 104. The pressure modulator 134 may be configured to apply a positive pressure within the urinary collection system 100. The positive pressure may be configured to "flush" the urinary waste out of the urinary collection system 100. The urinary waste may be configured to travel from an area of high pressure created by the positive pressure to an area of relatively lower pressure, such as out through the waste outlet 104. Additionally or alternately, the pressure modulator 134 is configured to impose a negative pressure differential between a first pressure within the urinary waste receptacle 102 and a second pressure external to the urinary waste receptacle 102. In one implementation, the pressure modulator 134 may decrease the first pressure from an idle first pressure to an active first pressure; that is, the pressure modulator 134 can increase the pressure. The pressure modulator 134 may be configured to maintain a sealing interface between the receptacle 102 and the skin of the genital region of the user U.

The pressure modulator 134 may be any suitable pump, e.g., with a reduced size. In one implementation, the pressure modulator 134 is a Kamoer KLC2 Food Grade 6v DC Micro Mini Diaphragm Pump. In another implementation, the pressure modulator 134 is a Piezoelectric Micro Pump.

Various specific implementations of urinary collection systems and urinary waste receptacles are provided in FIGS. 2 through 11. General features that are present in multiple implementations may not be described in each implementation.

Figure 2:
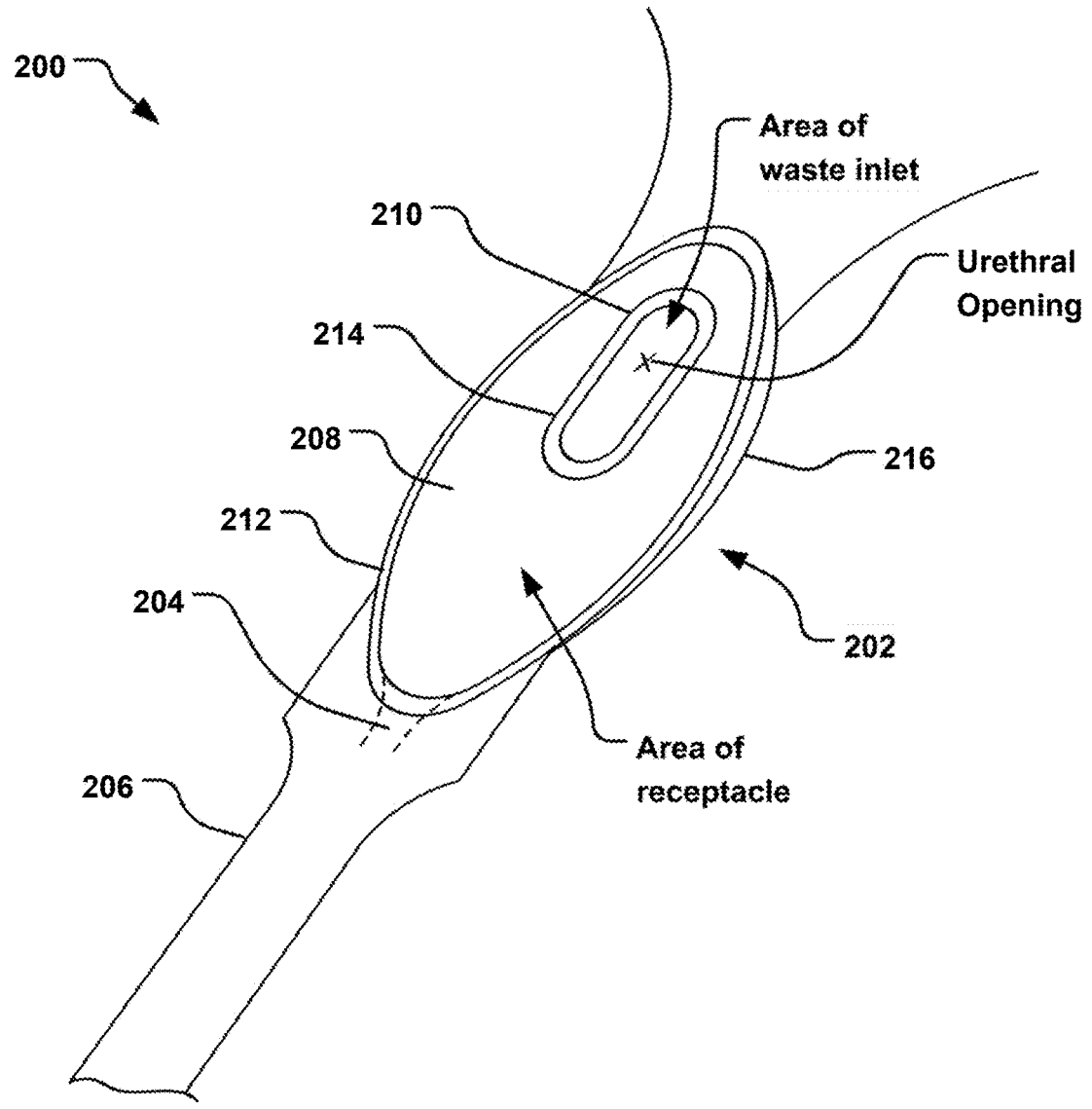
FIG. 2 is a schematic perspective view of an example urinary collection system.
Figure 3:
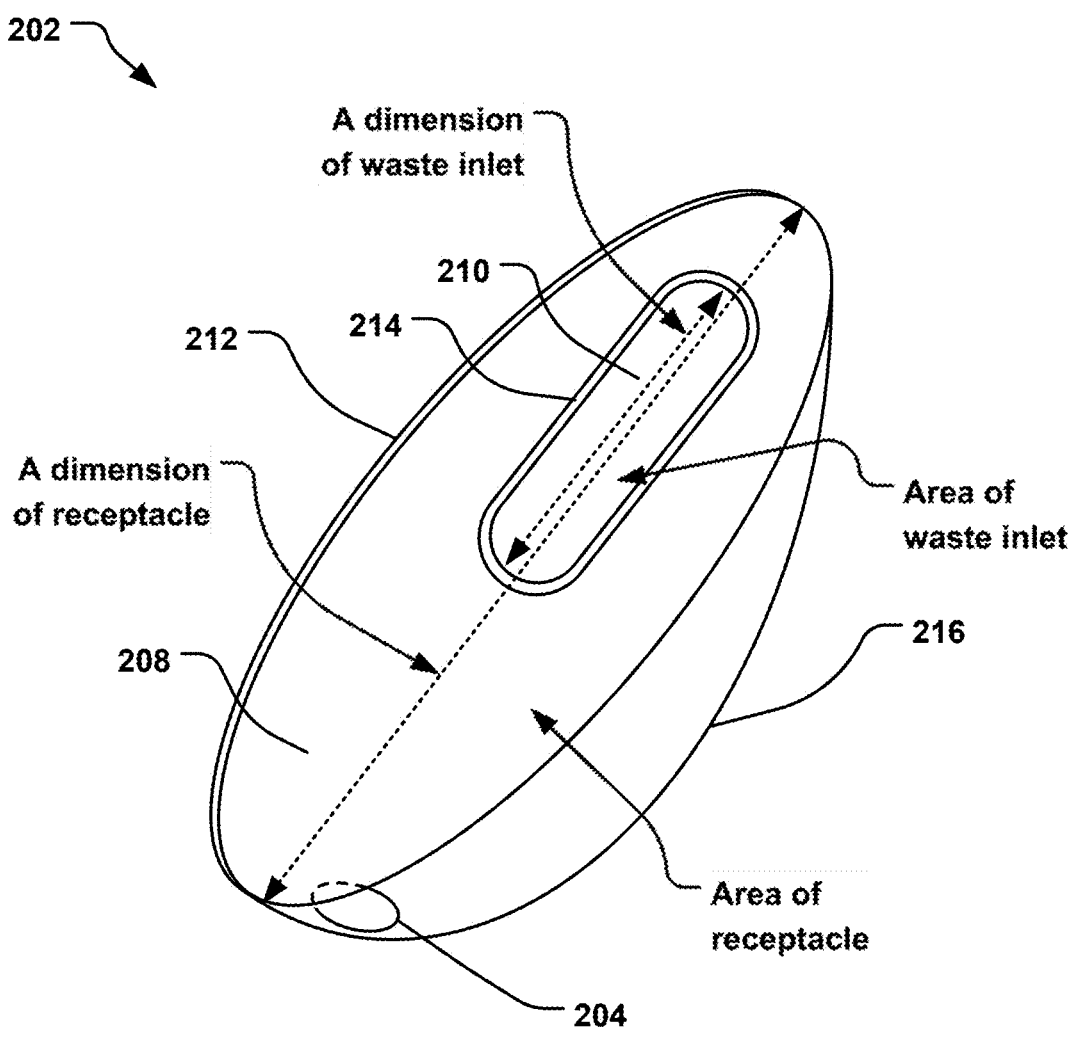
FIG. 3 is a perspective view of the urinary waste receptacle of the system of FIG. 2.

FIGS. 2 and 3 illustrate an example urinary collection system 200 having a urinary waste receptacle 202 and a harness 206.

The urinary waste receptacle 202 has a substantially concave dome-shaped shell 216 and an opposite wall 208 that at least partially defines an interior collecting volume. Through the wall 208 is an aperture forming a urinary waste inlet 210 to be aligned with the urethral opening when the receptacle 202 is properly positioned when in use. The inlet 210 is configured to be positioned in close proximity to, and preferably aligned with, the urethral opening to collect the urinary waste therefrom during urination by the user. Present in either or both the shell 216 and the wall 208 is a waste outlet 204.

The shell 216 may take the shape of a hemisphere or any of a variety of other shapes. In one implementation, the shell 216 narrows towards the waste outlet 204, forming a funnel to the waste outlet 204, which is proximate the perineum. The shell 216 may be contoured to accommodate the user's physical anatomy; for example, the shell 216 may narrow to comfortably accommodate the thighs of the user. Similarly, the wall 208 may be contoured to accommodate the user's physical anatomy, for example, having a concave shape contouring to an external genital region. The shell 216 and the wall 208 are generally not parallel to each other, but can have a generally similar shape and contour.

The receptacle 202 can be provided in several shapes and sizes to accommodate different body shapes and sizes.

No matter the shape or size of the receptacle 202, the area of the urinary waste inlet 210 is smaller than a maximum area of the urinary waste receptacle 202, e.g., the cross-sectional area of the urinary waste inlet 210 is smaller than a maximum cross-sectional area of the urinary waste receptacle 202. The area or cross-sectional area of the urinary waste inlet 210 may be no more than 50%, 30%, 20%, 10%, or even 5% of the maximum area or cross-sectional area of the urinary waste receptacle 202. A dimension, such as a diameter, of the urinary waste inlet may be no more than 50%, 30%, 20%, or even 10% of a dimension, such as a diameter, of the receptacle 202. The urinary waste inlet 210 is large enough to encompass at least the urinary opening, optionally the vaginal opening, and optionally the clitoral region.

The urinary waste inlet 210 may have a perimeter at least partially defined by a deformable seal 214. The deformable seal 214 is an interface between the receptacle 202 and the skin of the genital region, which may include the urethral opening and/or the vulva, and may include some surrounding skin; the interface may be substantially sealed. Examples of suitable materials of the deformable seal 214 include silicon, rubber, or a foam (open cell (e.g., sponge) or closed cell), which may be a natural or polymer material. The seal 214 may be absorbent or include a wicking material.

The wall 208 opposite the shell 216 (the wall 208 having the inlet 210 therethrough) may be flat (planar) or somewhat concave, to better contour to the user's anatomy. The wall 208 may be shaped to align with the natural curvature of the genital region; this may enhance the comfort of wearing the urinary waste receptacle 202 and the urinary collection system. The wall 208 may be configured to reside over the vulva.

The perimeter of the receptacle 202, e.g., at the juncture of the wall 208 and the shell 216, may include a flexible and/or compressible seal 212 or fenders that decrease discomfort from wearing the device. The seal 212 may be soft, compressible (squishy), or have other qualities configured to reduce discomfort such as chafing and pinching. Examples of suitable materials of the deformable seal 212 include silicon, rubber, or a foam (open cell or closed cell), which may be a natural or polymer material. The seal 212 may be absorbent (e.g., a sponge).

The wall 208 and the shell 216 define the interior collecting volume and provide a substantially enclosed space for urinary waste to flow through with a decreased risk of spilling out of the urinary waste receptacle 202. The urinary waste receptacle 202 is shaped to direct waste toward the outlet 204 by utilizing a geometry that promotes urinary waste being guided toward the waste outlet 204 using gravity while the user is seated or standing. In one implementation, the urinary waste receptacle 202 is configured to promote substantially laminar flow of the urinary waste through the urinary waste receptacle 202 towards the outlet 204. Typically, the flow of waste from the inlet 210 to the outlet 204 is direct, unimpeded or unobstructed by any structure, so that the flow out from the outlet 204 is at the same or similar rate as the flow in via the inlet 210; although the term "collecting volume" may be used, waste is not retained long-term in the volume but instead exits the volume at close to the same rate as it enters the volume.

However, the interior volume of the shell 216 and the wall 208 are configured to provide a volume for urinary waste in the event that the waste outlet 204 cannot immediately remove the present urinary waste. By having the available volume, a backup of urinary waste will not impede the user's ability to urinate and the urinary waste will be less likely to leak out of the deformable seal 212. Further, by having the available volume, backup of the urinary waste through the urinary waste inlet 210 is inhibited; such backflow would be messy, unsanitary, and unpleasant.

The interior collecting volume of the urinary waste receptacle 202 may be sufficiently large to accommodate any backup of urinary waste. The volume may be less than a full urinary event as some urine can be removed via the waste outlet 204 during the urinary event. For example, if humans typically have a urination rate of about 0.6-1.2 liters per minute, then the waste outlet 204 may be able to transport at least 0.6-1.2 liters of waste per minute.

The collecting volume may be able to account for an estimated difference in inlet flow rate and outlet flow rate of urinary waste across the time of the urinary event. Depending on the urination rate, the internal volume of the urinary waste receptacle 202 may buffer between the inflow rate of urinary waste into the urinary waste inlet 210 and an outflow rate of urinary waste out of the waste outlet 204 by providing a volume in which the urinary waste can temporarily reside if the outflow rate of urinary waste out of the waste outlet 204 is less than the inflow rate of urinary waste into the urinary waste inlet 210. For example, if the inlet flow rate is estimated to be 1 liter per minute, and the outlet flow rate is estimated to be 0.8 liter per minute, and the duration of the urinary event is estimated to be thirty seconds, the volume of the urinary waste receptacle 202 may be at least 0.1 liter, although a greater volume would be desired for more margin.

Typically, the rate of flow of urinary waste into the receptacle 202 varies across the duration of the urinary event. To account for this, the configuration (e.g., shape) of the waste receptacle 202 and/or the outlet 204 can be designed to vary the outlet flow rate dependent on the volume of urine present in the urinary waste receptacle 202. In one implementation, the urinary waste receptacle 202 and waste outlet 204 have a shape that increases the outlet flow rate as the retained volume of waste increases.

The urinary waste receptacle 202, including the shell 216 and the wall 208, independently, can be made of a variety of materials (e.g., rubber, silicone, silicon rubber, plastic such as polyurethane). In one implementation, the shell 216 is semi-rigid with some flexibility or elasticity, to decrease discomfort from wearing the device or enhance the discreetness of the device. The wall 208 may be rigid, semi-rigid, or fully flexible or elastic. The perimeter of the shell 216 and/or the wall 208 may be rigid, optionally with a flexible or compressible surface, to enhance the seal between the device and the user.

In one implementation, the interface between the inlet 210 and the user is sealed or substantially sealed, e.g., by the deformable seal 214. A substantially sealed interface may be substantially water-resistant, substantially waterproof, etc., to mitigate the risk of liquid leakage across the interface.

As indicated above, the interior volume of the urinary waste receptacle 202 and is configured to remove the urinary waste from the interior volume of the receptacle 202, e.g., by its geometry and being guided by gravity and the pressure differential within the interior collecting volume caused by the flow of waste therethrough. Additionally or alternately, the flow through the receptacle 202 can be aided by a suction device. A surfactant on the interior surface of the receptacle 202 may promote laminar flow or substantially laminar flow of waste towards the waste outlet 204. Additionally or alternately, the inside surface of receptacle 202 may be treated with a surfactant or water-repellent configured to decrease tension between the waste and the inside surface of the receptacle 202 and increase the ability to repel or wick waste towards the waste outlet 204. In another implementation, the urinary waste receptacle 202 itself is at least partially made of a water-repellent material (e.g., polyvinyl chloride, polytetrafluoroethylene (PTFE), silicone).

The waste outlet 204 is an aperture and may be formed by a variety of rigid, semi-rigid, flexible, or elastic materials (e.g., rubber, silicone, liquid silicon rubber, plastic). The waste outlet 204 may have a cross-sectional area sufficiently large to be able to direct the waste out of the urinary waste receptacle 202 without any backup of waste in the receptacle 202.

In one implementation, the waste outlet 204 is configured to discretely exit the clothing of the user to, e.g., a drain. In another implementation, the urinary waste may be stored within the clothing of the user, such as in a container such as a bag. Such a container may be disposable or may be emptied manually by the user or another user. The container may include other features, such as a component that reduces the scent of the urinary waste from the container.

The receptacle 202 can be configured to provide a woman the ability to urinate while in a standing position. The waste outlet 204 may connect to an outlet pipe that directs waste to a desired disposal. The outlet pipe may include an outlet pipe cap that caps the outlet pipe when disposal is not desired, to prevent leakage. The outlet pipe may also be kinked when not in use to prevent leakage. The outlet pipe may be configured to direct waste out of the clothing of the user. In one implementation, the outlet pipe may be configured to fit through the zipper of the user's pants, or another gap in the user's pants. The outlet pipe may be flexible and/or expandable. The outlet pipe may be folded when not in use for storage. The outlet pipe may also be made of a flexible accordion-style pipe or hose, which can be compressed when not in use for storage. The user or another user may direct the outlet pipe to dispose of the waste. The outlet pipe allows the urinary collection system to function as a stand to pee (STP) device, if desired, allowing the user to urinate while standing up; standing provides better sanitary conditions, protection, and peace of mind for some users, as outdoor bathroom facilities and congested facilities may be unsanitary.

In one implementation, the outlet pipe may take the form of a tube temporarily positioned within the urinary waste receptacle 202. The tube may be flexible and/or expandable. The tube may be configured to expand while urinary waste is present inside the tube. The tube may reside inside the urinary waste receptacle 202 and may be able to be pulled or extended out of the urinary waste receptacle. In this implementation, the tube may enable the urinary collection system to function as an STP device.

In another implementation, the urinary waste receptacle 202 may have an internal tubular structure configured to transport the urinary waste from the urinary waste inlet 210 to the urinary waste outlet 204. The tubular structure may be configured to expand or inflate with the presence of urinary waste. In one implementation, the internal tubular structure takes the form of a balloon, pipe or tube within the urinary waste receptacle 202 and may conform to the concave shape of the shell 216 to facilitate rapid laminar flow of the waste to the outlet 204. The internal tubular structure may be able to extend outside of the urinary waste receptacle 202.

The urinary waste receptacle 202 can be held in proper position on the user by the harness 206, which may take the form of an undergarment such as underwear. The harness 206 may be adjustable to allow the user to adjust the location of the urinary waste receptacle 202 with respect to the harness 206. This may allow the user to tune the location of the urinary waste inlet 210 to substantially align with the urethral opening.

Figure 4:
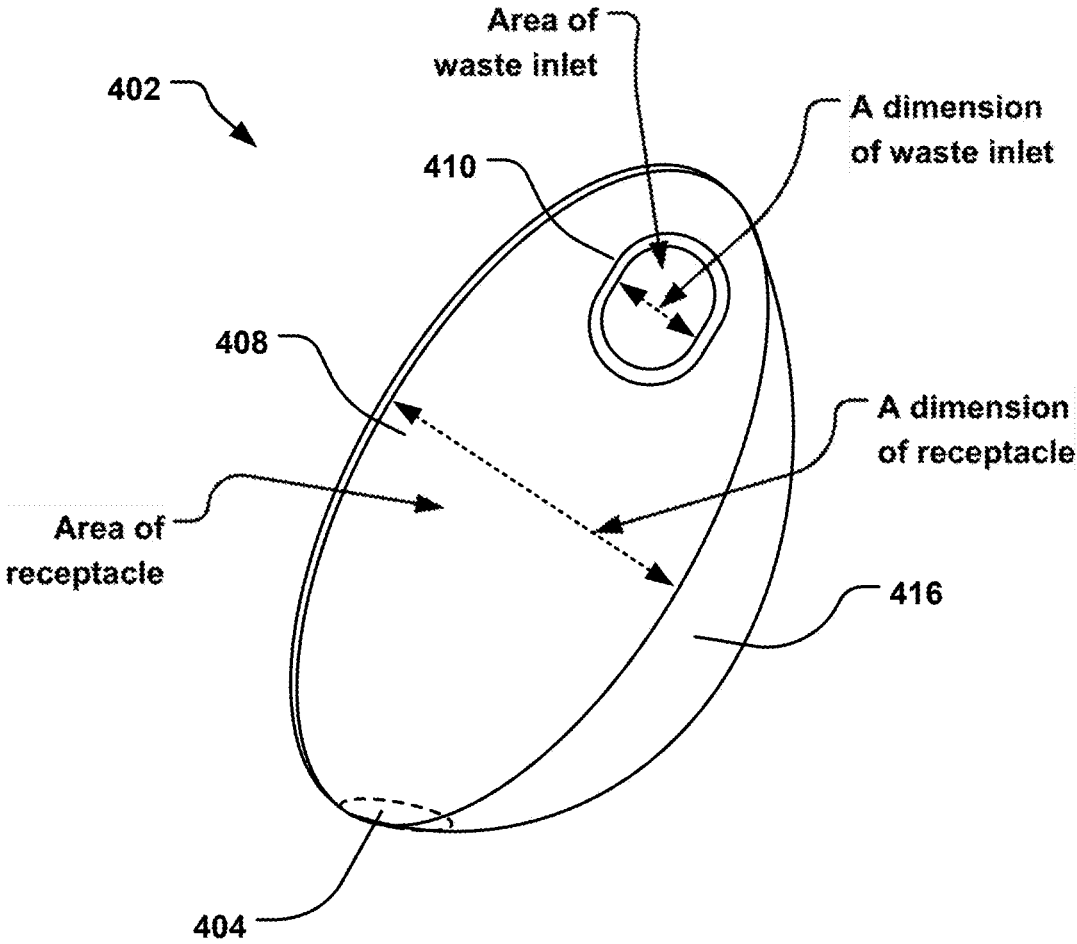
FIG. 4 is a schematic perspective view of another example urinary waste receptacle with a small urinary waste inlet.

FIG. 4 illustrates an example urinary waste receptacle 402 similar to the receptacle 202 of FIGS. 2 and 3, however with a small urinary waste inlet 410 through the wall 408 opposite the shell 416. Waste entering via the inlet 410 exits the receptacle 402 via the outlet 404, due to, at least, gravity. After exiting the waste outlet 404, the urinary waste may be directed to a container that stores the waste.

Figure 5:
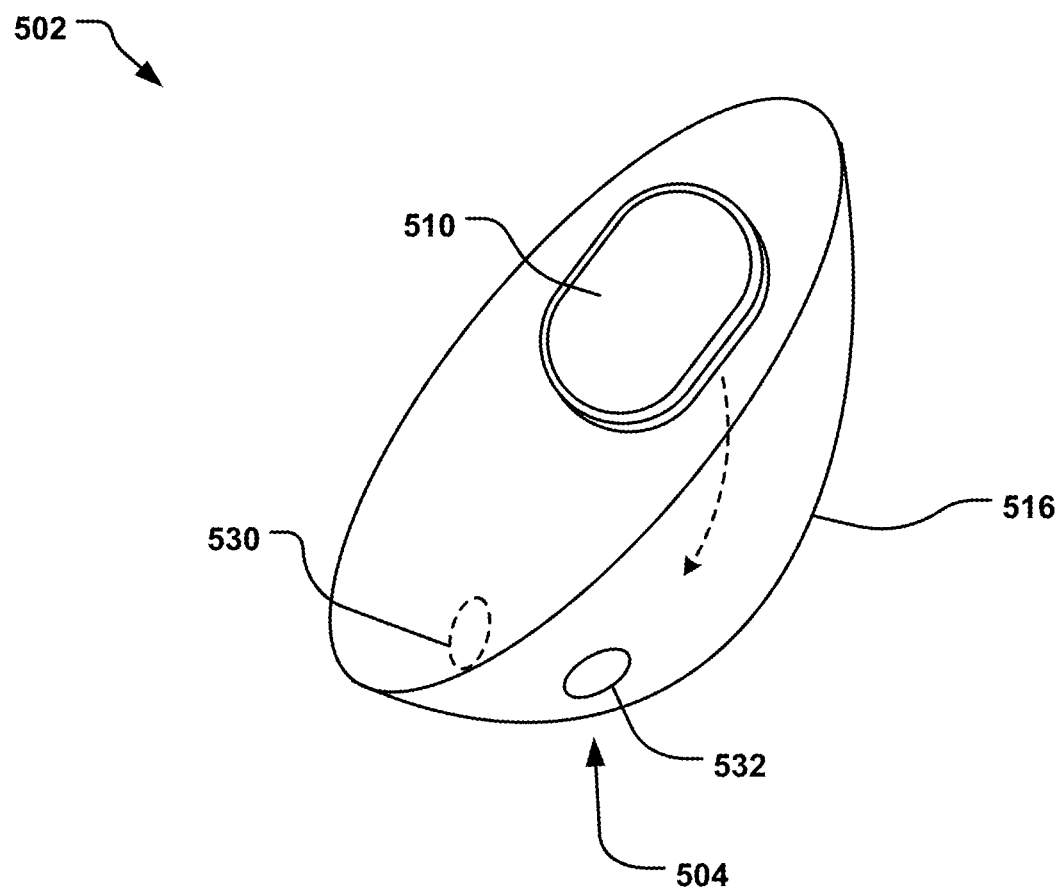
FIG. 5 is a schematic side view of a urinary waste receptacle with a first waste outlet and a second waste outlet.

FIG. 5 illustrates a side view of an example urinary waste receptacle 502 having a waste inlet 510 and a waste outlet 504 for the removal of urinary waste from the interior volume of the receptacle 502.

In this implementation, the waste outlet 504 has two outlets, a first waste outlet 530 and a second waste outlet 532, each formed by an aperture in the shell 516 and fluidly connected to the interior volume of the receptacle 502. The first waste outlet 530 and the second waste outlet 532 may lead to different containers; for example, the first waste outlet 530 may direct urinary waste to a first container (e.g., attached to one leg of the user) and the second waste outlet 532 may direct urinary waste to a second container (e.g., attached to the other leg of the user). Having two waste outlets provides a safety mechanism, e.g., in case one outlet becomes occluded.

Figure 6:
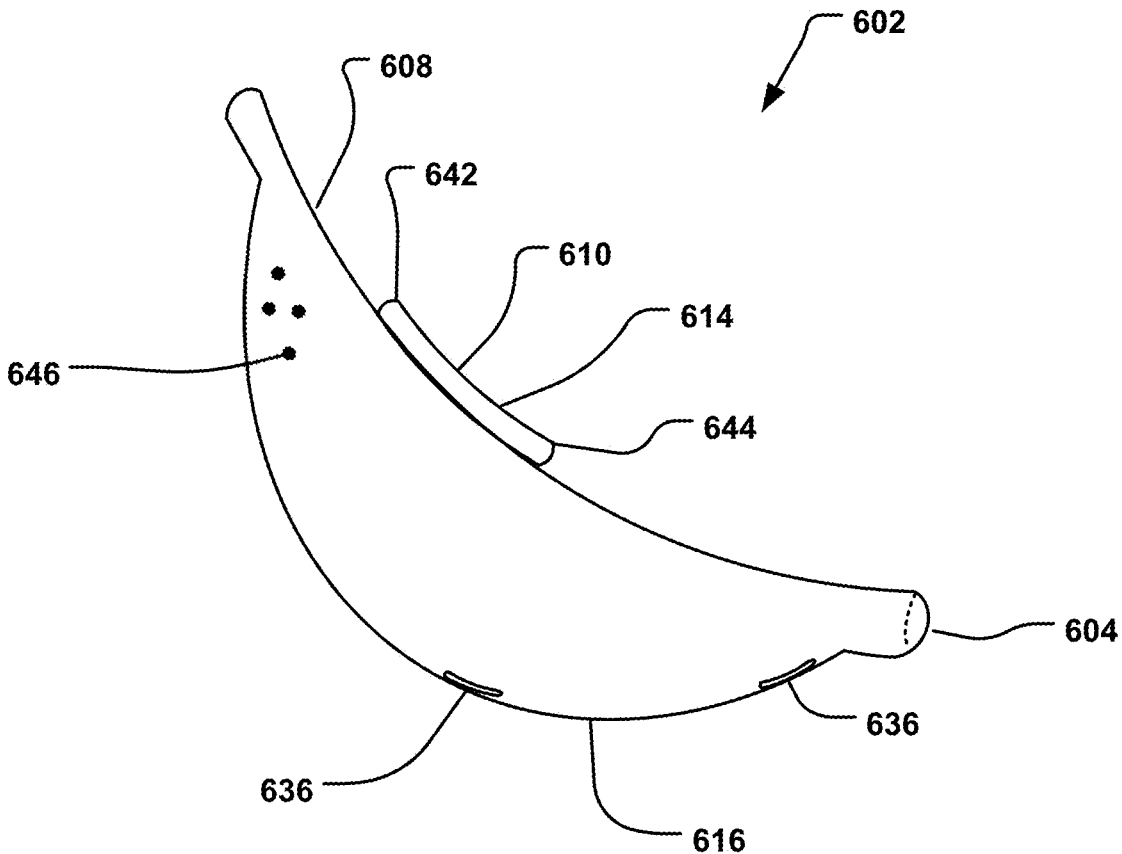
FIG. 6 is a schematic side view of another example urinary waste receptacle with a waste sensor and vents.

FIG. 6 illustrates an example urinary waste receptacle 602 with at least one waste sensor and at least one vent. As with previous examples, the urinary waste receptacle 602 includes a substantially concave dome-shaped shell 616 and an opposite wall 608 forming an internal volume, with a urinary waste inlet 610 into the internal volume of the receptacle 602 and a urinary waste outlet 604 from the internal volume. As with other receptacles described herein, the receptacle 602 does not store or retain the urinary waste, but provides a conduit for passage from the inlet 610 to the outlet 604.

At least one waste sensor 636 is positioned in the receptacle 602 to detect a presence of the urinary waste within the urinary waste receptacle 602; the sensor 636 may be, for example, in or on the surface of the concave shell 616. In an alternate implementation, the waste sensor 636 may be positioned in or proximate to the waste outlet 604. The waste sensor 636 may be a moisture sensor, a thermal sensor, a conductivity sensor, an electrolyte sensor, a pH sensor, or any other sensor that can detect the presence of urinary waste.

Upon detection of the presence of the urinary waste by the waste sensor 636, a tightening mechanism may be activated to increase the engagement of the urinary waste receptacle 602 against the user. In one implementation, the urinary waste receptacle 602 is pressed against the user by decreasing the first pressure from the idle first pressure to the active first pressure using the pressure modulator (not shown in FIG. 6; see the pressure modulator 134 of FIG. 1). In another implementation, the urinary waste receptacle 602 is pressed against the user by tightening straps of the harness, the straps being attached to the urinary waste receptacle 602 and configured to fit around a limb or torso of the user. In yet another implementation, the pressure modulator or other suction device can remove urinary waste from the receptacle 602 when the waste sensor 636 detects the presence of the urinary waste within the receptacle 602.

In any of these situations, the waste sensor 636 may trigger an audible and/or visual alarm for a caregiver.

The waste sensor 636 may be connected to a communication network, either wired or wirelessly, e.g., to notify the user or another (e.g., someone assisting the user) that urine is detected in the urinary waste receptacle 602 and that subsequent action may be needed (e.g., emptying a collection container). The urinary collection system may be configured to be connected to a network via, e.g., a mobile phone network, Wi-Fi, Bluetooth® communication protocol, ZigBee® communication protocol or other protocol to communicate with other devices, such as a device at a remote location, such as a nurses station.

As with other designs herein, the urinary waste inlet 610 may have a perimeter at least partially lined with a deformable seal 614, which may be configured to protrude towards the user to increase the pressure between the deformable seal 614 and the user.

The deformable seal 614 has a first end or side 642 configured to be closer to the mons pubis and a second end or side 644 configured to be opposite the side 642 and closer to the perineum, when the receptacle 602 is properly positioned for use by a user. The second side 644 of the deformable seal 614 may apply more pressure to the genital region of the user than the first side 642. In one implementation, the second side 644 is configured to protrude more towards the user than the first side 642 of the seal 614 to increase the pressure the second side 644 applies to the user below the urethral opening. This may allow urinary waste that travels downward from the influence of gravity to be better collected by the deformable seal 614.

Upon detection of the presence of the urinary waste by the waste sensor 636, the deformable seal 614 may be configured to enter an active state, e.g., where the deformable seal 614 is enhanced. The deformable seal 614 may grow in size or protrude further toward the user. In one implementation, the deformable seal 614 is made of a material that expands when heated. In another implementation, the deformable seal 614 is made of an electroactive polymer or another material that expands when stimulated by an electric field.

In another implementation, the deformable seal 614 protrudes by activating an electromagnet system. The electromagnet system may comprise an electromagnet, an opposing magnet, and a connecting medium. The electromagnet is configured to be turned on when the electromagnet system is activated. The opposing magnet may be orientated so the north pole of the opposing magnet is pointed towards the side of the electromagnet that functions as a north pole when the electromagnet is turned on. In another implementation, the opposing magnet may be orientated so the south pole of the opposing magnet is pointed towards the side of the electromagnet that functions as a south pole when the electromagnet is turned on. The electromagnet and opposing magnet are configured to repel each other when the electromagnet is turned on. The connecting medium may be elastic, flexible, or stretchy. The connecting medium may pull the electromagnet and the opposing magnet together when the electromagnet is off but allow the opposing magnet to push away and move somewhat away from the electromagnet when the electromagnet is turned on. The electromagnet may be housed in the concave panel 620 surrounding the urinary waste inlet 610, and the opposing magnet and connecting medium may be located on the side of the concave panel 620 configured to be closer to the user. The deformable seal 614 may be configured to reside between the opposing magnet and the user.

Not shown in FIG. 6, but the receptacle 602 may have a perimeter compressible seal to decrease discomfort from wearing the device. Similar to the seal 614 around the inlet 610, the perimeter seal may be configured to enter an active state, e.g., where the seal is enhanced, when the presence of urinary waste is detected by the waste sensor 636.

For these implementations, the receptacle 602 would include appropriate elements (e.g., heater, electric field generator, magnets and/or magnetic field generator, appropriate controller, etc.) to implement these designs.

The urinary waste receptacle 602 also has one or more vents 646 configured to support air circulation into and out of the urinary waste receptacle 602. The configuration of the vents 646 may be designed to decrease the risk of urinary waste escaping the urinary waste receptacle 602 via the vents 646. In this context, the configuration of the vents 646 may include the structure and elements of the vents 646, the positioning/location of the vents 646, and the orientation of the vents 646. The vents 646 may be located towards the top of the shell 616, the top of the shell 616 being the side of the shell 616 closer to the mons pubis than the perineum, to decrease the risk that urinary waste under the influence of gravity can escape from the vents 646. The vents 646 may also contribute to pressure regulation within the urinary waste receptacle 602.

The vents 646 can include structure and elements configured to decrease the risk that urinary waste under the influence of gravity can escape from the vents 646. For instance, the vents 646 may include louvers or slats fixed at an angle that decreases the risk of urinary waste escaping. The vents 646 may form a crooked, zig-zag, curved, or otherwise indirect path from the internal volume to the outside of the urinary waste receptacle 602, which may allow for air to travel through the vents 646 but may impede the ability of urinary waste to splash out via the vents 646. Additionally or alternately the vents 646 may include a barrier made of a material that allows air to pass through but inhibits passage of liquid (e.g., Gore-Tex™ or other PTFE).

Figure 7:
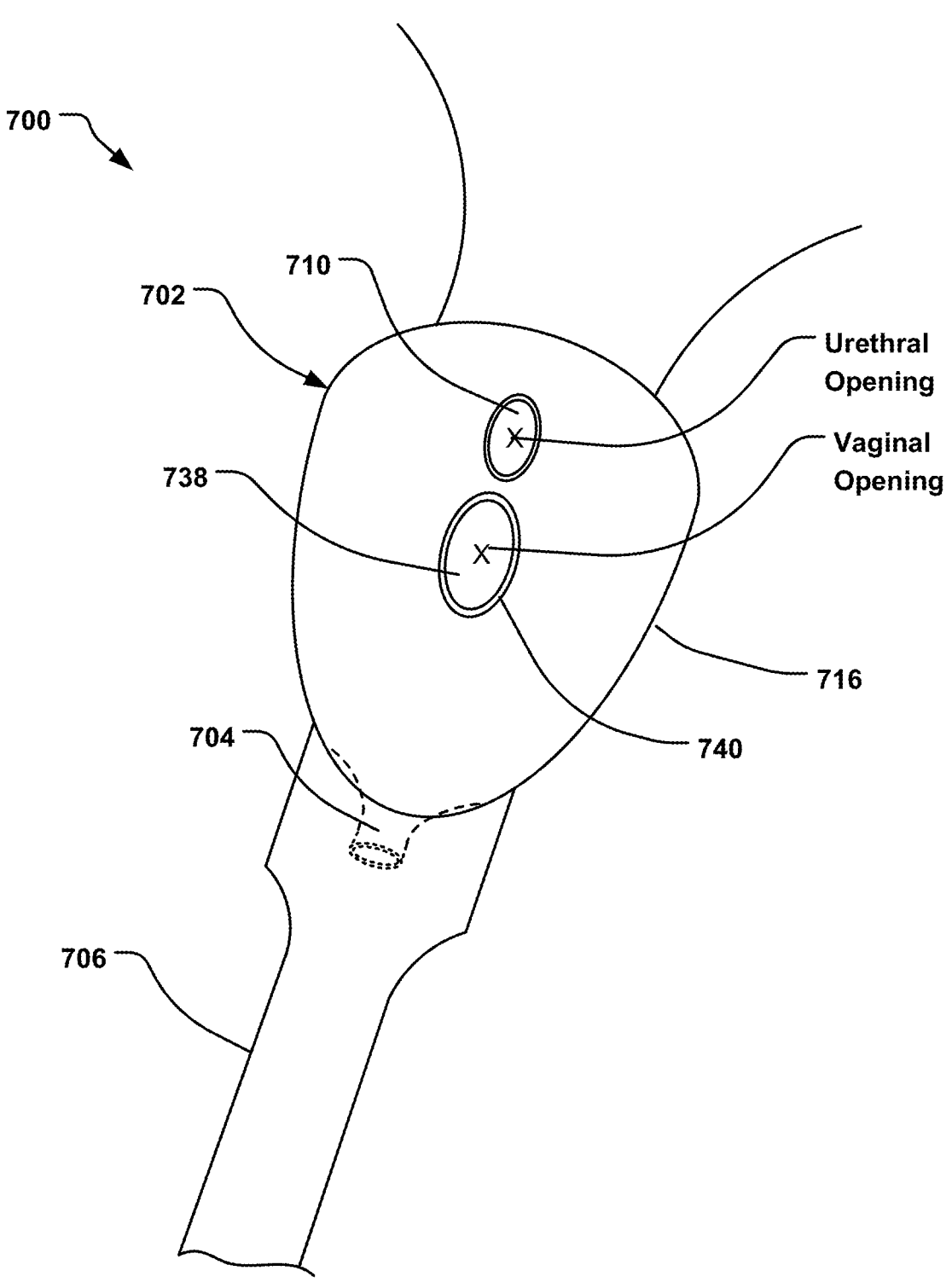
FIG. 7 is a schematic perspective view of an example urinary collection system with a second waste inlet.

FIG. 7 illustrates an example urinary collection system 700 having a second waste inlet into the urinary waste receptacle. As with previous examples, the system 700 has a urinary waste receptacle 702 includes a substantially concave dome-shaped shell 716 at least partially forming an internal volume, with a urinary waste inlet 710 into the internal volume of the receptacle 702 and a urinary waste outlet 704 from the internal volume. The system 700 includes a harness 706 connected to the receptacle 702 to position and hold the receptacle 702 proximate a user.

The urinary waste receptacle 702 has a second waste inlet 738 separate from the urinary waste inlet 710 with a cross-sectional area of the second urinary waste inlet 738 smaller than a maximum cross-sectional area of the urinary waste receptacle. The urinary waste inlet 710 and/or the second waste inlet 738 are located in the concave wall of the receptacle 702 opposite the shell 716. The second waste inlet 738 is configured to be positioned to collect waste not collected by the urinary waste inlet 710; in some implementations, the second waste inlet 738 is configured to align with the vaginal opening (e.g., for collection of menstruation waste). The second waste inlet 738 may or may not have a perimeter lined with a second deformable seal 740. The second waste inlet 738 may include an absorbent and/or wicking material.

In one implementation, an additional structure such as a dam, baffle or the like may be present inside the urinary waste receptacle 702 to direct urinary waste from either or both inlets 710, 738 toward the waste outlet 704 without hindering the flow of the waste.

In another implementation, the urinary waste receptacle 702 may have an internal tubular structure connected to each inlet 710, 738 configured to transport the urinary waste from the urinary waste inlets 710, 738 to the urinary waste outlet 704. The internal tubular structures may be configured to expand or inflate with the presence of urinary waste. The two tubular structures may have the same or different physical dimensions, properties, and configured to have the same or different flow volumes and/or pressures therethrough. The tubular structures may conform to the concave shape of the shell 716 to facilitate rapid laminar flow of the waste to the outlet 704.

Figure 8:
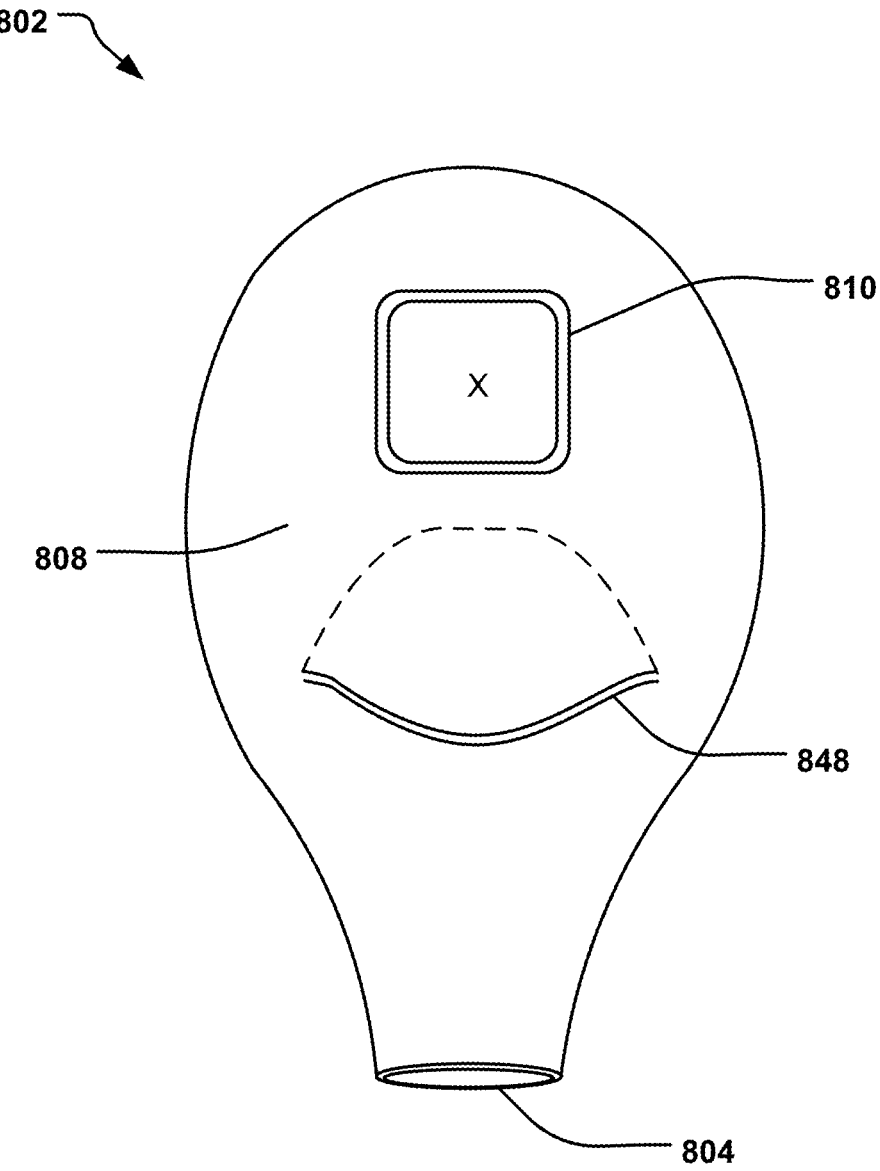
FIG. 8 is a schematic top view of another example urinary waste receptacle configured to provide space for a user's thighs.

FIG. 8 illustrates an example urinary waste receptacle 802 configured to better fit within the space between the user's thighs. The receptacle 802 has a tapered shape, being more narrow proximate the waste outlet 804. A dam-like structure 848 is present on the exterior surface of the wall 808, to catch waste that may not have entered the receptacle 802 via the inlet 810. Additionally in this example, the urinary waste inlet 810 has a generally rectangular or square shape.

Figure 9:
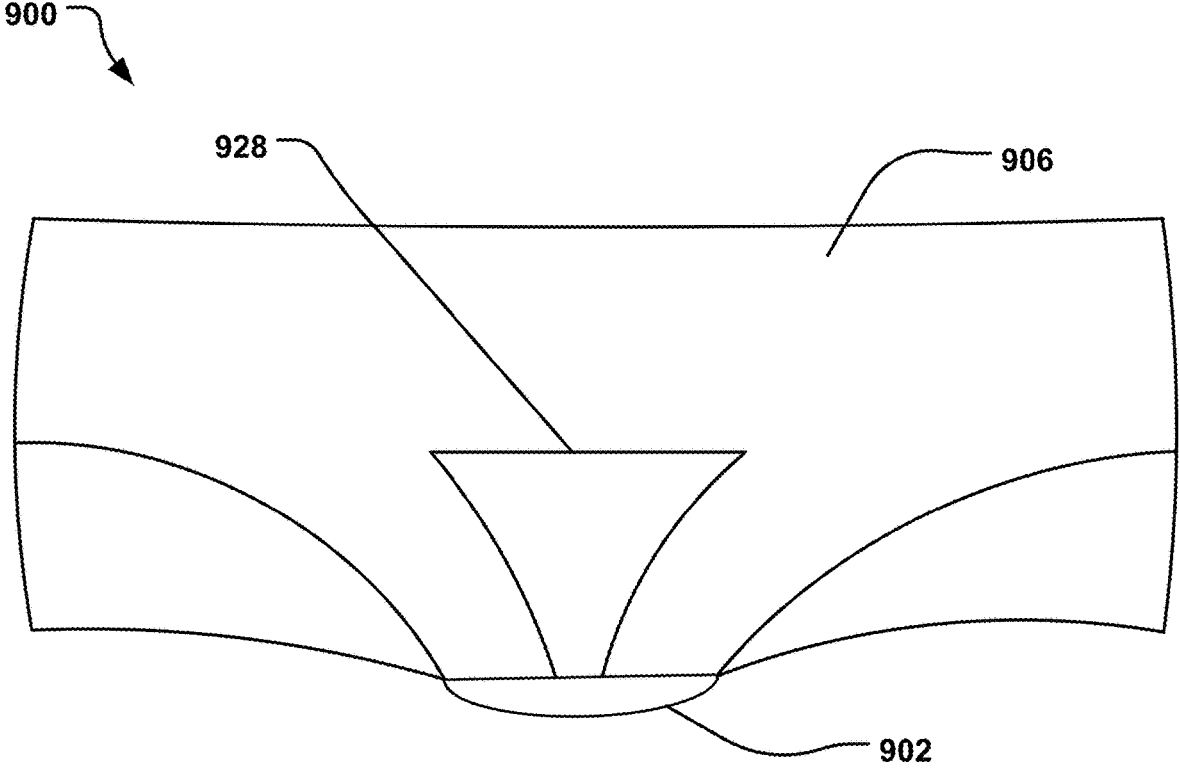
FIG. 9 is a schematic rear view of an example system having a harness and a urinary waste receptacle.

FIG. 9 shows an example urinary collection system 900 with a rear view of an example harness 906, in this implementation shaped similar to underwear. Similar to previously described harnesses, the harness 906 is configured to position and retain a urinary waste receptacle 902 in close proximity to a user's genital region, particularly the urethral opening. In this implementation, the harness 906 is configured to not cover the anus, such that defecation is not inhibited or blocked by the harness 906. The harness 906 has an aperture or a gap 928 therein, positioned over or in close proximity to the anus when the harness 906 is properly positioned on a user. The harness 906 may include additional material or straps around the thighs of the user to situate and/or stabilize the urinary waste receptacle 902; these straps may be similar to the configuration found in a climbing harness.

Figure 10:
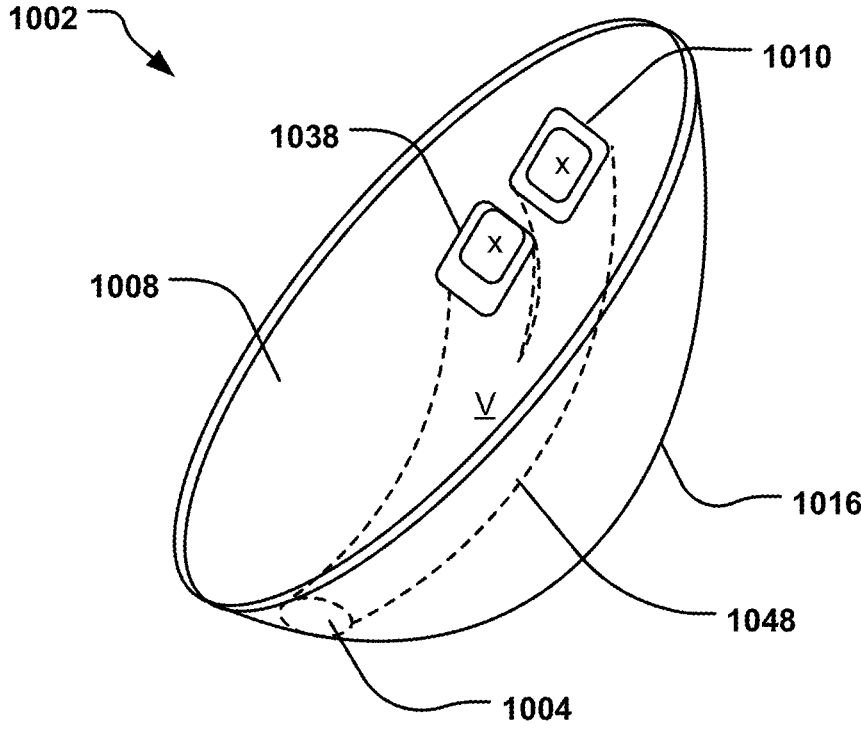
FIG. 10 is a schematic perspective view of an example urinary waste receptacle with a second waste inlet and additional structure.

Turning to FIG. 10, the urinary waste receptacle can include one or more internal structures, such as baffles, configured to influence the path of urinary waste through the receptacle. The structure may be configured to prevent urinary waste from sloshing or splashing and/or to inhibit urinary waste from escaping the receptacle via the urinary waste inlet or another opening besides the urinary waste outlet.

FIG. 10 illustrates an example urinary waste receptacle 1002 with a waste inlet 1010 and also a second waste inlet 1038 in the wall 1008 opposite the concave domed shaped shell 1016. Present within the shell 1016 is a flow diverter 1048 that facilitates the flow of urinary waste from both of the inlets 1010, 1038 to an interior volume V within the shell 1016 and on to the outlet 1004. The arcuate structure of the flow diverter 1048 inhibits reverse flow back to the inlets 1010, 1038. The flow diverter 1048 may be a semi-rigid structure or may be flexible, such as a balloon or membrane, to facilitate transport the urinary waste from the urinary waste inlets 1010, 1038 to the urinary waste outlet 1004. The inlets 1010, 1038 may be essentially the same area or they may be different in size; if different, the first inlet 1010 will typically be larger.

Figure 11:
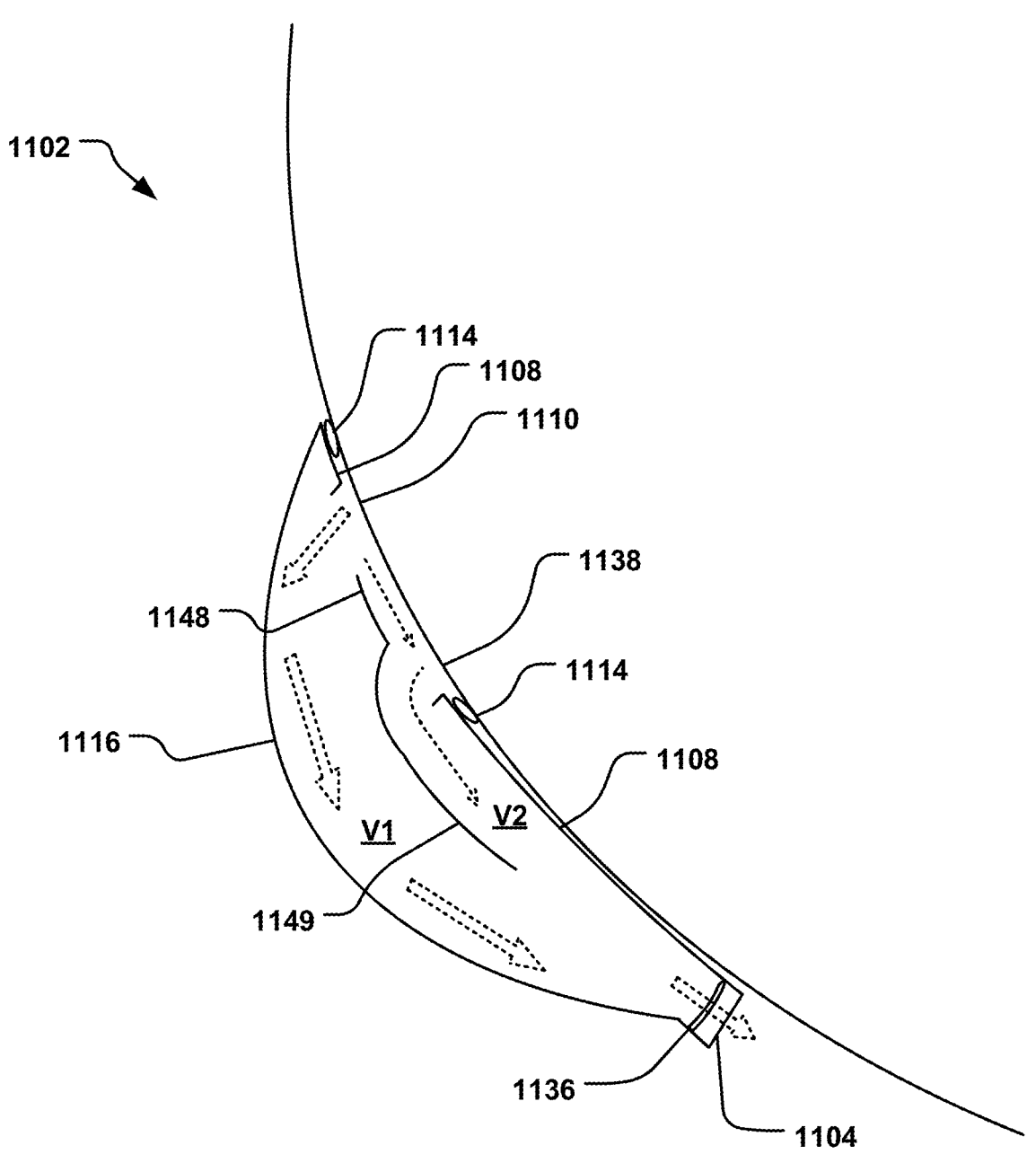
FIG. 11 is a schematic perspective side view of an example urinary waste receptacle showing an example liquid stream path.

FIG. 11 illustrates another example urinary waste receptacle 1102 with a flow diverter 1148 that divides the interior volume into two conduits, the receptacle 1102 shown in relation to a user's body. This receptacle 1102 has a waste inlet 1110 into a first volume V1 defined by the dome-shaped shell 1116 and a second waste inlet 1138 into a second volume V2, both volumes V1, V2 fluidly connected to the outlet 1104. The flow diverter 1148 extends from the inlets 1110, 1138 to the outlet 1104, where it has a lower portion; the flow diverter 1148, together with the shell 1116 and the opposite wall 1108, define the two generally tubular volumes V1, V2 Unlike the waste receptacle 1002 of FIG. 10, which has two distinct apertures through the wall 1008 forming the inlets 1110, 1038, the receptacle 1102 has the two waste inlets 1110, 1138 defined by a single aperture in the wall 1108. With this design, waste that may not pass through the inlet 1110 (e.g., it may dribble along the skin surface due to gravity) is caught and diverted toward the outlet 1104 by the structure of the wall 1108 proximate the second inlet 1138. Also with this design, because a urinary event may have a higher flow rate and pressure at the beginning than at the end of the event, the initial (stronger) stream may enter via the inlet 1110 into the volume V1 and the decreased (weaker) stream may enter via the inlet 1138 into the volume V2.

In either situation, because the volume V1 may receive the majority of the waste flow, the volume V1 may have a greater flow rate and pressure therethrough and therein than the volume V2.

The wall 1108, proximate the second inlet 1138, may have a conformable seal 1114 or other dam-like structure around at least a portion of the inlet 1138 to direct the waste flow through the inlet 1138 and into the interior volume V2. In some implementations, the seal 1114 is not present proximate the location of clitoris (when the receptacle 1102 is properly seated against a user). Additionally or alternately, the wall 1108 itself may not be present proximate the clitoris, to inhibit or avoid applying pressure on the clitoris.

In the shown design, the lower portion 1149 of the flow diverter 1148 at least partially distinguishes the two separate volumes V1, V2. In other implementations, the lower portion 1149 may not be present or may have a shorter structure, thus allowing waste from the second inlet 1138 to mix with that from the first inlet 1110.

Through both inlets 1110, 1138, the flow of waste is directed to the outlet 1104 (at least via gravity) unobstructed but only guided by the flow diverter 1148; in other designs, the flow from each inlet 1110, 1138 may flow to a separate outlet. The flow of waste from the inlets 1110, 1138 to the outlet 1104 is direct, preferably in a rapid, laminar nature. The liquid flow dynamics through the two volumes V1, V2 may be the same or may differ.

A sensor 1136 is present at the outlet 1104 to detect the presence of urinary waste passing through the outlet 1104.

Figure 12:
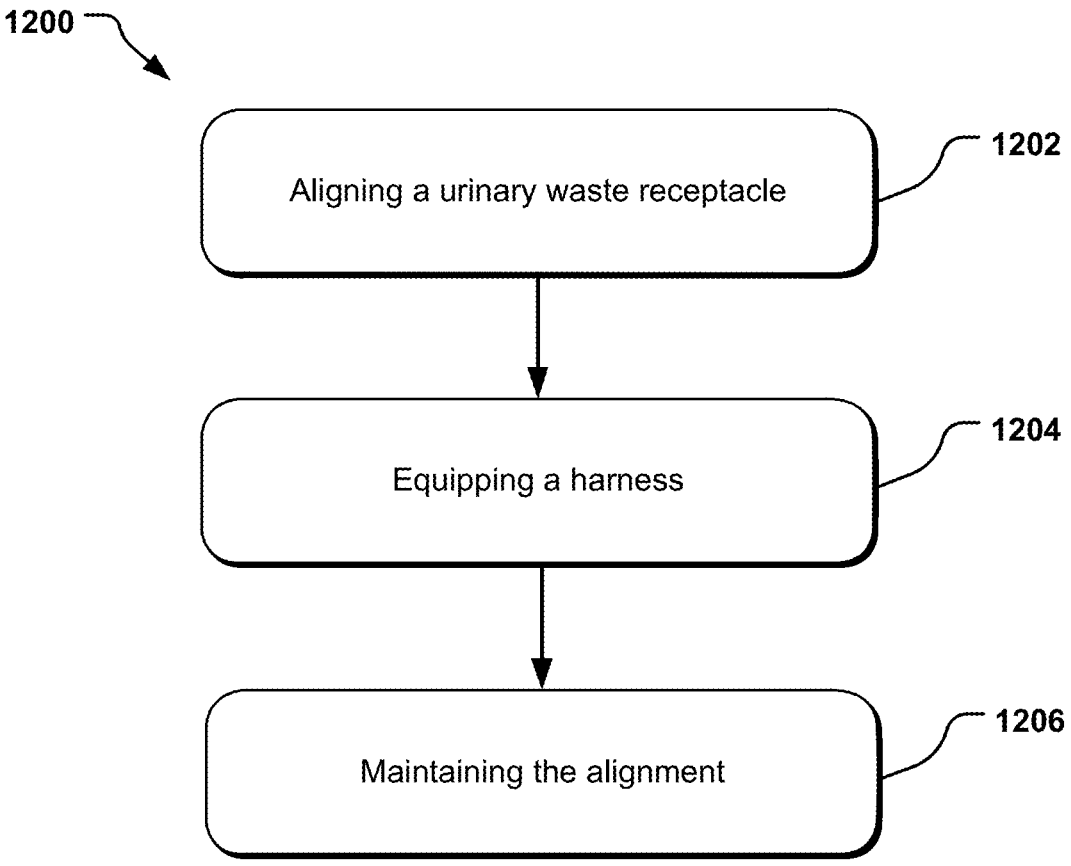
FIG. 12 is a stepwise diagram of a method of using a system for collecting and removing urinary waste from a user.

FIG. 12 illustrates, stepwise, a method 1200 for using a urinary collection system, e.g., as described herein and variations thereof, for collecting and removing urinary waste from a user. The method 1200 includes an aligning operation 1202, an equipping operation 1204, and a maintaining alignment operation 1206.

The aligning operation 1202 aligns a urinary waste receptacle with or in close proximity to a urethral opening of the user, the urinary waste receptacle having a urinary waste inlet that is smaller than a maximum cross-sectional area of the receptacle. The urinary waste inlet may have a perimeter at least partially lined with a deformable seal. The urinary waste receptacle is configured to be positioned to collect the urinary waste from the urethral opening during urination by the user. A waste outlet extends from the urinary waste receptacle. The waste outlet is configured to remove the urinary waste from the urinary waste receptacle. The urinary waste receptacle may be any of those described herein, and variations thereof.

The equipping operation 1204 equips a harness on and at least partially around the user. The harness is attached to the urinary waste receptacle and is configured to pull the receptacle against a genital region of the user to form seal between the receptacle and the skin of the genital region around the urethral opening of the user. The urinary waste receptacle remains external to the user.

The maintaining alignment operation 1206 maintains the alignment of the urinary waste receptacle for at least a portion of urination by the user to collect urine into the urinary waste receptacle. The portion of urination may be the complete duration of urination, a small timeframe within that duration, or another time period that includes urination into the urinary waste receptacle. The alignment may be fully maintained or partially maintained; a partial maintaining of alignment may include the alignment being slightly off of the desired positioning but still somewhat functional to collect urine in the urinary waste receptacle.

Although not shown in FIG. 12, the method 1200 may also include a sealing operation, which substantially seals the interface between the deformable seal and the genital region.

The method may also include a first actuating operation, which actuates a pressure modulator, e.g., positioned in line with the waste outlet. The pressure modulator is configured to impose a negative pressure differential between a first pressure within the urinary waste receptacle and a second pressure external to the urinary waste receptacle. The pressure modulator is configured to maintain the interface between the receptacle and the skin of the genital region. The idle first pressure is less than the second pressure.

The method may also have a second actuating operation, which actuates a waste sensor positioned within the urinary waste receptacle. The waste sensor is configured to detect a presence of the urinary waste within the urinary waste receptacle. Upon detection of the presence of the urinary waste by the waste sensor, a tightening mechanism is activated to pull the urinary waste receptacle against the user.

The method can further include a decreasing operation. A decreasing operation decreases the first pressure from an idle first pressure to an active first pressure to pull the urinary waste receptacle against the user.

The method can further include a tightening operation. The tightening operation tightens straps to pull the urinary waste receptacle against the user. The straps are attached to the urinary waste receptacle and configured to fit around a limb or torso of the user.

The method can further include a collecting operation. The collecting operation collects waste not collected by the urinary waste inlet with a second waste inlet. The second waste inlet is separate from the urinary waste inlet and configured to align with the vaginal opening. The second waste inlet is configured to be positioned to collect waste not collected by the urinary waste inlet.

The method can further include a ventilating operation. The ventilating operation ventilates air through the urinary waste receptacle with one or more vents. The one or more vents are configured to support air circulation into and out of the urinary waste receptacle. The configuration of the vents is configured to decrease the risk of urinary waste escaping the urinary waste receptacle via the vents.

From the foregoing description and examples, it will be appreciated that specific embodiments and implementations of the invention have been described herein for purposes of illustration and that various modifications may be made without deviating from the scope of the invention. For example, any of the waste receptacles described herein, and variations thereof, could be used without a harness; for example, the receptacle could be supported by, attached to, or integrated with the user's underwear. Accordingly, the invention is not limited except as by the appended claims.

Although the technology has been described in language that is specific to certain structures and materials, it is to be understood that the invention defined in the appended claims is not necessarily limited to the specific structures and materials described. Rather, the specific aspects are described as forms of implementing the claimed invention. Because many embodiments of the invention can be practiced without departing from the spirit and scope of the invention, the invention resides in the claims hereinafter appended.

Various features and details have been provided in the multiple designs described above and shown in the figures. It is to be understood that any features or details of one design may be utilized for any other design, unless contrary to the construction or configuration. Any variations may be made.

The above specification and examples provide a complete description of the structure and use of exemplary implementations of the invention. The above description provides specific implementations. It is to be understood that other implementations are contemplated and may be made without departing from the scope or spirit of the present disclosure. The above detailed description, therefore, is not to be taken in a limiting sense. While the present disclosure is not so limited, an appreciation of various aspects of the disclosure will be gained through a discussion of the examples provided.

Unless otherwise indicated, all numbers expressing feature sizes, amounts, and physical properties are to be understood as being modified by the term "about," whether or not the term "about" is immediately present. Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass implementations having plural referents, unless the content clearly dictates otherwise. As used in this specification and the appended claims, the term "or" is generally employed in its sense including "and/or" unless the content clearly dictates otherwise.

Spatially related terms, including but not limited to, "bottom," "lower", "top" "upper", "beneath", "below", "above", "on top", "on," etc., if used herein, are utilized for ease of description to describe spatial relationships of an element(s) to another. Such spatially related terms encompass different orientations of the device in addition to the particular orientations depicted in the figures and described herein. For example, if a structure depicted in the figures is turned over or flipped over, portions previously described as below or beneath other elements would then be above or over those other elements.

The invention claimed is:

1. A system for collecting and removing urinary waste from a user, the system comprising:

a urinary waste receptacle configured to remain external to a genital region of the user with no portion of the waste receptacle entering the urethral opening, the waste receptacle comprising:

a shell and a concave wall defining an interior volume with a deformable and compressible seal present at a perimeter of the concave wall;

a urinary waste inlet through the concave wall fluidly connected to the interior volume with a perimeter of the inlet at least partially lined with a deformable seal, wherein an area of the urinary waste inlet is smaller than a maximum area of the urinary waste receptacle, with the urinary waste inlet configured to align with a urethral opening of the user when the receptacle is positioned in use in relation to a user, and with the urinary waste receptacle configured to collect the urinary waste from the urethral opening during urination by the user; and a flow diverter in the interior volume dividing the interior volume into two tubular conduits extending from the waste inlet to a waste outlet defined by an aperture in the shell to facilitate flow of the urinary waste through the urinary waste receptacle from the waste inlet towards the waste outlet.

2. The system of claim 1, wherein the urinary waste receptacle further comprises a second waste inlet through the concave wall separate from the urinary waste inlet in close proximity to the urinary waste inlet to receive waste that is not collected by the urinary waste inlet.

3. The system of claim 1 further comprising a harness attached to the urinary waste receptacle and configured to pull the deformable seal against a genital region of the user to form an interface between the deformable seal and skin of the genital region around the urethral opening of the user.

4. The system of claim 3 further comprising a waste sensor positioned within the urinary waste receptacle and configured to detect a presence of the urinary waste within the urinary waste receptacle.

5. The system of claim 4 further comprising a tightening mechanism operably connected to the harness, wherein upon detection of the presence of the urinary waste by the waste sensor, the tightening mechanism is activated to pull the urinary waste receptacle against the user.

6. The system of claim 1, further comprising a waste sensor positioned within the urinary waste receptacle and configured to detect a presence of the urinary waste within the urinary waste receptacle.

7. The system of claim 1, wherein the urinary waste receptacle is configured to promote substantially laminar flow of the urinary waste through the urinary waste receptacle towards the waste outlet.

8. The system of claim 1, further comprising:
a pressure modulator positioned in-line with the waste outlet and configured to impose a negative pressure differential between a first pressure within the urinary waste receptacle and a second pressure external to the urinary waste receptacle, the pressure modulator configured to maintain an interface between the deformable seal and skin of the genital region, wherein the first pressure is less than the second pressure.

9. A system for collecting and removing urinary waste from a user, the system comprising:
a urinary waste receptacle defined by a concave dome-shaped shell and an opposite concave wall, the shell and the wall defining an interior volume;
a deformable and compressible perimeter seal at a juncture of the shell and the wall;
an aperture in the wall defining a urinary waste inlet fluidly connected to the interior volume, the aperture having a dimension no greater than 50% of a maximum dimension of the concave wall, with a compressible dam-like structure at least partially around the aperture; and
a flow diverter comprising a tubular structure in the interior volume dividing the interior volume into two conduits extending from the urinary waste inlet to a waste outlet defined by an aperture in the shell.

10. The system of claim 9 further comprising a harness attached to the urinary waste receptacle and configured to position the waste receptacle against a genital region of the user.

11. The system of claim 9 further comprising a waste sensor positioned within the urinary waste receptacle.

12. The system of claim 9, wherein the flow diverter comprises a tubular structure extending from the urinary waste inlet to the waste outlet, and the urinary waste receptacle further comprises:
a second aperture in the wall separate from the aperture to receive waste that is not collected by the urinary waste inlet; and a second tubular structure within the interior volume extending from the second aperture to the waste outlet.

13. A system for collecting and removing urinary waste from a user, the system comprising:
a urinary waste collecting means configured to remain external to the user with no portion of the collecting means entering the urethral opening, the collecting means having a concave shell defining an internal volume, a deformable and compressible perimeter seal, a urinary waste inlet with a perimeter at least partially lined with a deformable seal and a waste outlet formed by an aperture through the collecting means, and a flow diverter having a tubular structure in the volume dividing the volume into two conduits extending from the urinary waste inlet to the waste outlet to facilitate flow of the urinary waste through the urinary waste collecting means from the urinary waste inlet towards the waste outlet, wherein an area of the urinary waste inlet is smaller than a maximum area of the urinary waste collecting means; and
means for retaining the urinary waste receptacle in a position to collect the urinary waste from a urethral opening during urination by the user.

14. The system of claim 13, further comprising sensing means for detecting presence of urinary waste within the urinary waste receptacle.

15. A method of collecting and removing urinary waste from a user, the method comprising:
aligning externally a urinary waste receptacle having a urinary waste inlet with a urethral opening of the user, the urinary waste receptacle defined by a concave dome-shaped shell and an opposite concave wall, the shell and wall defining an interior volume and having a deformable and compressible perimeter seal therearound, with the waste inlet formed by an aperture in the wall fluidly connected to the interior volume, the aperture having a deformable dam-like structure at least partially therearound, with the urinary waste receptacle further having a flow diverter having a tubular structure in the interior volume to divide the interior volume into two conduits extending from the urinary waste inlet to a waste outlet defined by an aperture in the shell to facilitate flow of the urinary waste through the urinary waste receptacle;
equipping a harness at least partially around the user, wherein the harness is attached to the urinary waste receptacle and configured to position the waste receptacle external to and against a labial region of the user; and
maintaining an alignment of the urinary waste receptacle for at least a portion of urination by the user to collect urine into the urinary waste receptacle.

16. The method of claim 15, wherein upon detection of presence of the urinary waste by a waste sensor within the urinary waste receptacle, pulling the urinary waste receptacle against the user.

17. The method of claim 15, further comprising:
collecting waste not collected by the urinary waste inlet with a second waste inlet, wherein the second waste inlet is separate from the urinary waste inlet, wherein the second waste inlet is configured to be positioned to collect the urinary waste not collected by the urinary waste inlet.

18. The system of claim 1 wherein the flow diverter defines two tubular volumes within the interior volume of the shell.

* * * * *